United States Patent
Chen et al.

(10) Patent No.: US 11,541,752 B2
(45) Date of Patent: Jan. 3, 2023

(54) INTELLIGENT IDENTITY-AUTHENTICATION ALCOHOL DETECTOR

(71) Applicant: Shenzhen Well Electric Co., Ltd., Guangdong (CN)

(72) Inventors: Zhi Chen, Guangdong (CN); Dong Chen, Guangdong (CN); Zebin Chen, Guangdong (CN); Yung Chan, Guangdong (CN)

(73) Assignee: Shenzhen Well Electric Co., Ltd., Shenzhen (CN)

( * ) Notice: Subject to any disclaimer, the term of this patent is extended or adjusted under 35 U.S.C. 154(b) by 651 days.

(21) Appl. No.: 16/659,547

(22) Filed: Oct. 21, 2019

(65) Prior Publication Data

US 2020/0376959 A1 Dec. 3, 2020

(30) Foreign Application Priority Data

May 29, 2019 (CN) .......................... 201910459350.7

(51) Int. Cl.
  *B60K 28/06* (2006.01)
  *G06K 9/00* (2022.01)
  *G06V 40/16* (2022.01)
  *G01N 33/497* (2006.01)

(52) U.S. Cl.
  CPC ......... *B60K 28/06* (2013.01); *G01N 33/4972* (2013.01); *G06V 40/16* (2022.01)

(58) Field of Classification Search
  CPC ..... B60K 28/06; G06V 40/16; G01N 33/4972
  See application file for complete search history.

(56) References Cited

U.S. PATENT DOCUMENTS

| 7,422,723 | B1 * | 9/2008 | Betsill | G01N 33/4972 422/549 |
| 9,709,582 | B1 * | 7/2017 | Gordon | G01N 33/582 |
| 2004/0239510 | A1 * | 12/2004 | Karsten | B60R 25/25 340/576 |
| 2019/0248281 | A1 * | 8/2019 | Fushimi | G05D 1/0061 |
| 2020/0367813 | A1 * | 11/2020 | Chen | A61B 5/4845 |
| 2022/0165089 | A1 * | 5/2022 | Mochizuki | G06V 40/166 |

FOREIGN PATENT DOCUMENTS

| CN | 207036748 U | * | 7/2017 |
| CN | 207036748 U | * | 2/2018 |

* cited by examiner

*Primary Examiner* — Zaihan Jiang

(57) ABSTRACT

The present application relates to the field of alcohol detection, and particularly to an intelligent identity-authentication alcohol detector. One technical solution comprises an intelligent identity-authentication alcohol detector, comprising a base, a mounting seat, and a connecting arm; the mounting seat is provided on the base, and a face information acquiring module is provided on the mounting seat; the connecting arm is rotatably provided on the base, and a breathing opening for alcohol detection is provided on the connecting arm; and the connecting arm is used for driving the breathing opening for alcohol detection to a position where the face information acquiring module acquires the face information of a subject. According to the technical solution of the present application, the face information acquiring module can constantly acquire the face information of a subject when the subject breathes into the breathing opening for alcohol detection, thereby preventing the subject from cheating.

9 Claims, 7 Drawing Sheets

INTELLIGENT IDENTITY-AUTHENTICATION ALCOHOL DETECTOR

CROSS REFERENCE TO RELATED APPLICATIONS

The present application claims the priority to Chinese Patent Application No. 201910459350.7 filed on May 29, 2019, which is incorporated herein by reference in its entirety for all purposes.

TECHNICAL FIELD

The present application relates to the field of alcohol detection, and in particular, to an intelligent identity-authentication alcohol detector.

BACKGROUND

An alcohol detector is an apparatus used for detecting whether alcohol is taken in a human body and how much alcohol is taken in. It can be used as a tool for detecting how much alcohol a driver has drunk by a traffic policeman on duty, so as to effectively reduce the occurrence of significant traffic accidents. An alcohol detector can also be used to detect the level of alcohol in the air expired from a human body on other occasions, for example, at some high-risk firms where it is prohibited to be on duty after drinking, so as to avoid personal casualties and significant property losses.

Further, a conventional alcohol detector has the function of face recognition, so as to recognize the face of a subject, preventing the subject from cheating during the process of alcohol detection in expired air. Particularly, a conventional alcohol detector comprises a base and a camera disposed on the base for acquiring the face information of a subject. A breathing opening for alcohol detection is further provided on the base.

However, the above conventional alcohol detector has the following defects in operation: both the camera and the breathing opening for alcohol detection are fixed on the base and close to each other, therefore, when a subject breathes into the breathing opening for alcohol detection, too close distance between the head of the subject and the camera prevents the camera from effectively acquiring the face information of the subject, increasing the risk of cheating by the subject when performing alcohol testing to the subject by using such alcohol detector.

BRIEF SUMMARY

In view of this, the present application provides an intelligent identity-authentication alcohol detector, mainly aiming to solve the technical problem of cheating by a subject during an alcohol detection since the camera cannot effectively acquire the face information of the subject when the subject breathes into the breathing opening for alcohol detection.

In order to achieve the above object, the present application mainly provides the following technical solutions:

one embodiment of the present application provides an intelligent identity-authentication alcohol detector comprising a base, a mounting seat, and a connecting arm;

the mounting seat is provided on the base, and a face information acquiring module is provided on the mounting seat;

the connecting arm is rotatably provided on the base, and a breathing opening for alcohol detection is provided on the connecting arm; and the connecting arm is used for driving the breathing opening for alcohol detection to a position where the face information acquiring module can acquire the face information of a subject, for the subject to breathe into the breathing opening for alcohol detection.

By adopting the above technical solution, since the connecting arm can be rotated relative to the base so that the positions of both the face information acquiring module on the mounting seat and the breathing opening for alcohol detection on the connecting arm can be adjusted relative to each other, the face information acquiring module can constantly keep acquiring the face information of a subject when the subject breathes into the breathing opening for alcohol detection, thereby preventing the subject from cheating.

In a further embodiment of the present application, a first lug and a second lug are disposed at interval on the side wall of the base;

the breathing opening for alcohol detection is provided at one end of the connecting arm, and the other end of the connecting arm is positioned between the first lug and the second lug;

one side of the connecting arm is connected to the first lug via a first rotary shaft, and the other side thereof is connected to the second lug via a second rotary shaft;

the axes of both the first rotary shaft and the second rotary shaft are collinear.

By adopting the above technical solution, the effect of rotating the connecting arm relative to the base can be achieved.

In a further embodiment of the present application, the alcohol detector can comprise a limiting structure;

the limiting structure is used for limiting the positions of the connecting arm, so that the connecting arm is rotated within a limited range.

By adopting the above technical solution, the connecting arm can drive the breathing opening for alcohol detection to move in a large distance, so as to meet demands of different subjects.

In a further embodiment of the present application, the limiting structure comprises a first limiting post provided at one side of the connecting arm, a first limiting slot extending along a first arc curve is provided on the first lug, the center of circle of the first arc curve is on the axis of the first rotary shaft, and the first limiting post is inserted into the first limiting slot, being used for being driven by the connecting arm to move along the first limiting slot;

and/or, the limiting structure comprises a second limiting post provided at the other side of the connecting arm, a second limiting slot extending along a second arc curve is provided on the second lug, the center of circle of the second arc curve is on the axis of the second rotary shaft, and the second limiting post is inserted into the second limiting slot, being used for being driven by the connecting arm to move along the second limiting slot.

By adopting the above technical solution, the cooperation of the first limiting post and the second post can achieve the effect of limiting the rotation of the connecting arm.

In a further embodiment of the present application, the alcohol detector comprises an alcohol detecting module and a displaying module;

the alcohol detecting module is provide on the connecting arm, and is used for detecting the level of alcohol in the air breathed into the breathing opening for alcohol detection;

the displaying module is provided on the mounting seat, and connected with the alcohol detecting module via a cable; the displaying module is used for receiving detected data from the alcohol detecting module and displaying the same;

wherein the cables are laid inside of the connecting arm and the base.

By adopting the above technical solution, laying the cables for connecting the alcohol detecting module and the displaying module inside the connecting arm and the base provides the effect of beautifying the appearance of the alcohol detector according to the present application.

In a further embodiment of the present application, when the first lug and the second lug are provided at interval on the side wall of the base and the other end of the connecting arm is rotatably connected between the first lug and the second lug, the inside of the base has a first wiring chamber for laying the cables therein, the side wall of the base is provided with a clearance opening for providing a clearance to the rotation of the connecting arm, the clearance opening being positioned between the first lug and the second lug;

a second wiring chamber for laying cables therein is provided inside the connecting arm, and a cable outlet in communication with the second wiring chamber is provided at the other end of the connecting arm;

the cable outlet extends from the end face of the other end of the connecting arm to the side of the connecting arm, so that the portion of the cable outlet located on the side of the connecting arm is opposite to the clearance opening when the connecting arm is rotated to a first limit position: and the portion of the cable outlet located on the end face of the connecting arm is opposite to the clearance opening when the connecting arm is rotated to a second limit position.

By adopting the above technical solution, when the connecting arm is rotated between the first limit position and the second limit position, the cables can be constantly positioned at the portion of the cable outlet opposite to the clearance opening, and thus the phenomenon of the cables being clipped and damaged can be avoided when the cables are positioned at the junction of the connecting arm and the base.

In a further embodiment of the present application, when the connecting arm is rotated to the first limit position, one end of the connecting arm approaches the mounting seat and abuts against the mounting seat.

By adopting the above technical solution, when the connecting arm is at the first limit position, the alcohol detector has a relatively compact overall structure, providing convenient transportation.

In a further embodiment of the present application, the connecting arm has a cover plate for opening/closing the second wiring chamber.

By adopting the above technical solution, when the cover plate is opened, it is convenient for an operator to lay cables inside the second wiring chamber.

In a further embodiment of the present application, a stand is provided on the base for providing a support for the mounting seat;

the mounting seat is rotatably provided on the stand so as to be connected with the base via the stand.

By adopting the above configuration, since both the mounting seat can also be rotated relative to the base, the position of the face acquiring module on the mounting seat can be adjusted, so as to be adapted for the purpose of face recognition during the process of breathing for alcohol detection of different subjects.

In a further embodiment of the present application, the alcohol detector further comprises an air mouthpiece used for breathing into the breathing opening for alcohol detection;

a recess is provided at one end of the connecting arm, the breathing opening for alcohol detection is provided at the bottom of the recess, and a buckle is provided on the side wall of the recess;

a snap-in groove is provided on the side of the air mouthpiece, one end of the air mouthpiece being inserted into the recess so that the buckle is snap connected with the snap-in groove.

By adopting the above technical solution, since the air mouthpiece is snap connected with the connecting arm, it can be disengaged from the connecting arm, so that the air mouthpiece can be replaced at any time when the air mouthpiece is damaged.

The above description is merely a summary of the technical solutions of the present application. For the purpose of better understanding the technical means of the present application and carrying out the same according to the disclosure of the present application, preferred embodiments of the present application are provided below and described in detail in connection with the drawings.

Reference numbers: 1. base; 2. mounting seat; 3. connecting arm; 4. stand; 5. air mouthpiece; 11. first lug; 12 second lug; 21. face information acquiring module; 31. buckle; 32. cover plate 101. first limiting slot; 102. second limiting slot 103. clearance opening: 301. cable outlet; 302. breathing opening for alcohol detection; 303. recess; 304. second wiring chamber; 501. snap-in groove; 100. alcohol detector.

DETAILED DESCRIPTION

The technical solutions defined in the embodiments of the application will be clearly and completely described below in combination with the drawings. It is to be noted that, if there are directional indications (for example, on/above, under/below, left, right, front, back . . . ) involved in the embodiments of the present application, the directional indications are merely intended for explaining the relative position relationship or moving relationship between components at some specific postures (for example, as shown in the figures), and if the specific postures are changed, these directional indications will be correspondingly changed therewith. In addition, if the expressions "first", "second" or the like are involved in the embodiments of the present application, they are merely intended for the purpose of description, and should not be construed as indicating or implying relative importance or the number of the technical features as mentioned. However, it can be indicated or implied that the technical features that are defined as "first", "second" or the like comprise at least one of such technical features.

Figure 1:
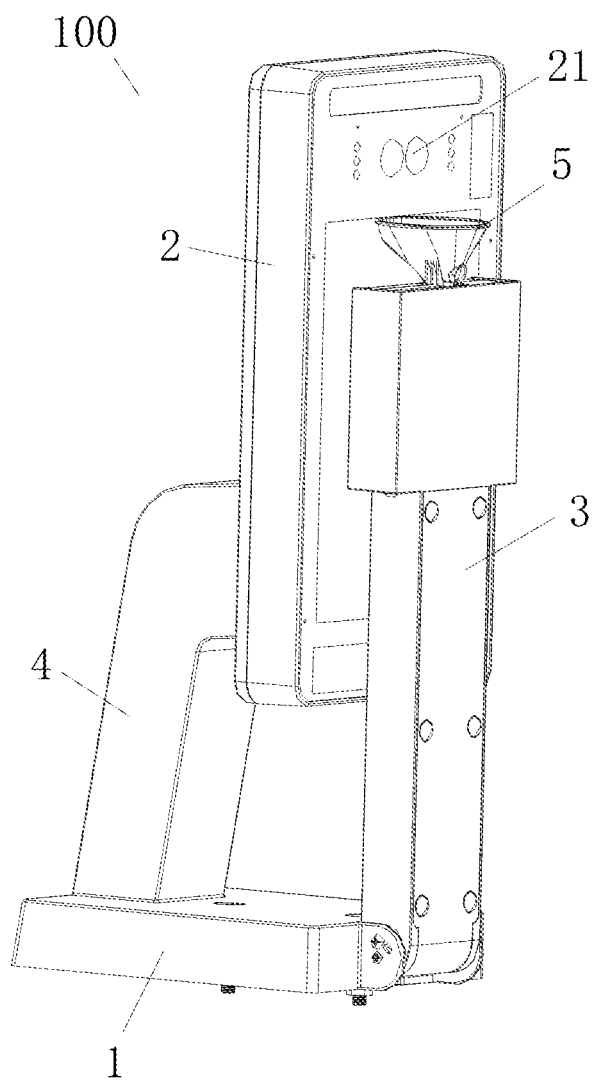
FIG. 1 is schematic structure view of an intelligent identity-authentication alcohol detector having closed connecting arm according to one embodiment of the present application.
Figure 2:
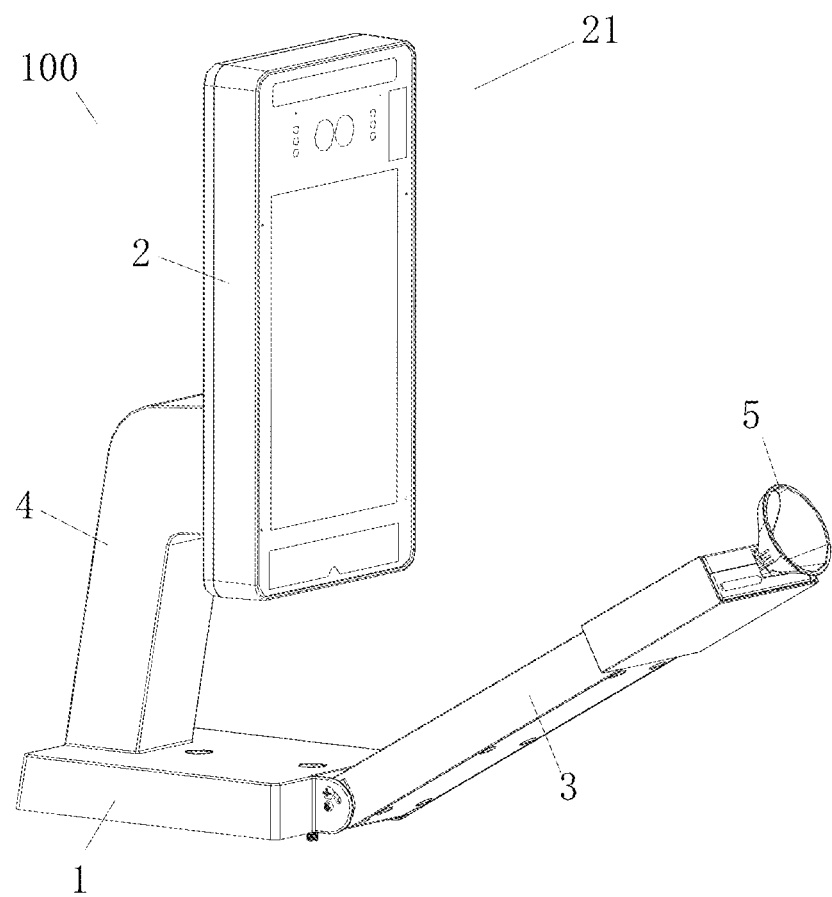
FIG. 2 is schematic structure view of an intelligent identity-authentication alcohol detector having opened connecting arm according to one embodiment of the present application.

As shown in FIG. 1, an identity-authentication alcohol detector 100 according to one embodiment of the present application comprises a base 1, a mounting seat 2, and a connecting arm 3. The mounting seat 2 is provided on the base 1. A face information acquiring module 21 is provided on the mounting seat 2, which is used for acquiring the face information of a subject. The connecting arm 3 is rotatably provided on the base 1. A breathing opening for alcohol detection 302 is provided on the connecting arm 3. The connecting arm 3 is used for driving the breathing opening for alcohol detection 302 to a position where the face information acquiring module 21 can acquire the face information of a subject, for the subject to breathe into the breathing opening for alcohol detection 302 (as shown in FIG. 2).

In the above technical solution, since the connecting arm 3 can be rotated relative to the base 1 so that the positions of both the face information acquiring module 21 on the mounting seat 2 and the breathing opening for alcohol detection 302 on the connecting arm 3 can be adjusted relative to each other, the face information acquiring module 21 can constantly keep acquiring the face information of a subject when the subject breathes into the breathing opening for alcohol detection, thereby preventing the subject from cheating.

Figure 3:
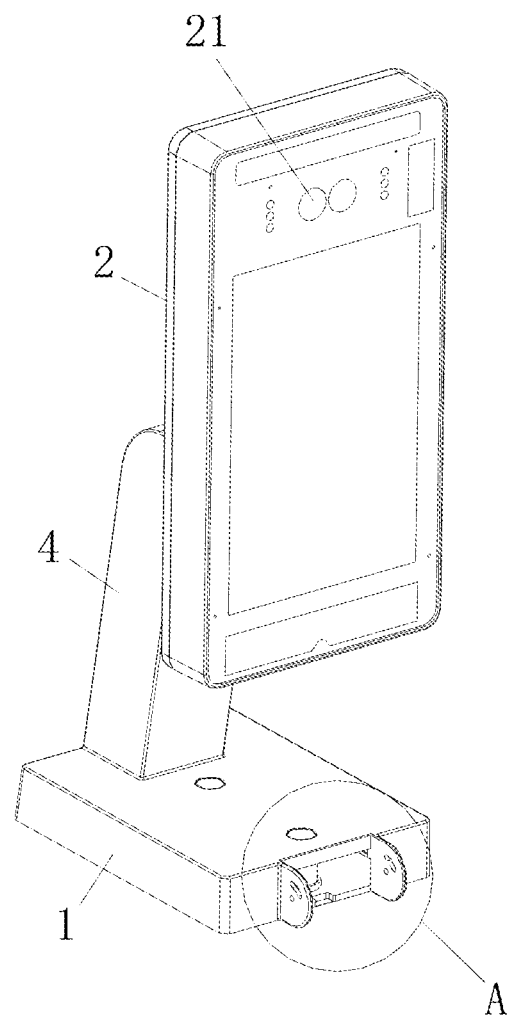
FIG. 3 is schematic structure view of an intelligent identity-authentication alcohol detector in which the connecting arm concealed according to one embodiment of the present application.
Figure 4:
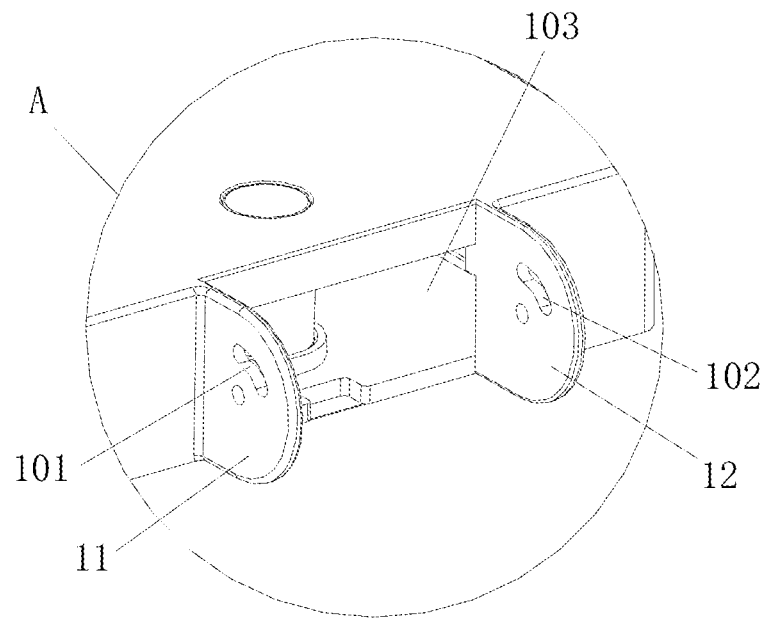
FIG. 4 is an enlarged schematic structure view of portion A in FIG. 3.

In order to achieve the function of rotating the connecting arm 3 relative to the base 1, a first lug 11 and a second lug 12 are disposed at interval on the side wall of the base 1, as shown in FIGS. 3 and 4. The breathing opening for alcohol detection 302 is provided at one end of the connecting arm 3, and the other end of the connecting arm 3 is positioned between the first lug 11 and the second lug 12. One side of the connecting arm 3 is connected to the first lug 11 via a first rotary shaft, and the other side thereof is connected to the second lug 12 via a second rotary shaft. The axes of the first rotary shaft and the second rotary shaft are collinear.

By adopting the above configuration, the connecting arm 3 can be rotated relative to the base 1 about the first rotary shaft and the second rotary shaft, and drive the breathing opening for alcohol detection 302 to move in a large distance since the breathing opening for alcohol detection 302 is disposed at the end of the connecting arm 3 departing from the base 1, thereby meeting the demands of different subjects.

Preferably, the first rotary shaft and the second rotary shaft can be a damping rotary shaft, so that the connecting arm 3 can be kept stationary at a post-rotation position, providing the effect of facilitating the breathing of a subject.

Further, the alcohol detector 100 can comprise a limiting structure. The limiting structure is used for limiting the positions of the connecting arm 3, so that the connecting arm 3 can be rotated within a limited range to decrease ineffective rotation of the connecting arm 3, and thus can be quickly rotated to the position for the subject to breathe.

In a particular application example, the limiting structure can comprise a first limiting post. The first limiting post is provided at one side of the connecting arm 3. As shown in FIG. 4, a first limiting slot 101 extending along a first arc curve is provided on the first lug 11. The center of circle of the first arc curve is on the axis of the first rotary shaft. The first limiting post is inserted into the first limiting slot 101. The first limiting post is used for being driven by the connecting arm 3 to move along the first limiting slot 101.

In particular, when the connecting arm 3 is rotated to a first limit position, the first limiting post abuts against one end of the first limiting slot 101, and when the connecting arm 3 is rotated to a second limit position, the first limiting post abuts against the other end of the first limiting slot 101, so as to stop the connecting arm 3 from keeping rotating, achieving the effect of limiting the position of the connecting arm 3.

The limiting structure can further comprise a second limiting post, which is provided at the other side of the connecting arm 3. As shown in FIG. 4, a second limiting slot 102 extending along a second arc curve is provided on the second lug 12. The center of circle of the second arc curve is on the axis of the second rotary shaft. The second limiting post is inserted into the second limiting slot 102. The second limiting post is used for being driven by the connecting arm 3 to move along the second limiting slot 102.

In particular, when the connecting arm 3 is rotated to a first limit position, the second limiting post abuts against one end of the second limiting slot 102, and when the connecting arm 3 is rotated to a second limit position, the second limiting post abuts against the other end of the second limiting slot 102, so as to stop the connecting arm 3 from keeping rotating, achieving the effect of limiting the position of the connecting arm 3.

The cooperation of the first limiting post and the second post can limit the positions of both sides of the connecting arm 3, providing a better stability.

The alcohol detector 100 according to the present application can further comprise an alcohol detecting module and a displaying module. The alcohol detecting module is provide on the connecting arm 3, and is used for detecting the level of alcohol in the air breathed into the breathing opening for alcohol detection 302. The displaying module is provided on the mounting seat 2, and connected with the alcohol detecting module via a cable. The displaying module is used for receiving and displaying detected data from the alcohol detecting module, for example, displaying the particular values of the detected results. In particular, as shown in FIGS. 1 and 2, the cables are laid inside of the connecting arm 3 and the base 1.

In the above example, providing both the alcohol detecting module and the breathing opening for alcohol detection 302 on the connecting arm 3 provides the effect of facilitating the connection therebetween. In addition, laying the cables for connecting the alcohol detecting module and the displaying module inside the connecting arm 3 and the base 1 provides the effect of beautifying the appearance of the alcohol detector 100 according to the present application.

The displaying module can be a display or the like.

It should be noted here that, the alcohol detecting module can be selected from conventional ones in the art, and thus is not described here.

Figure 5:
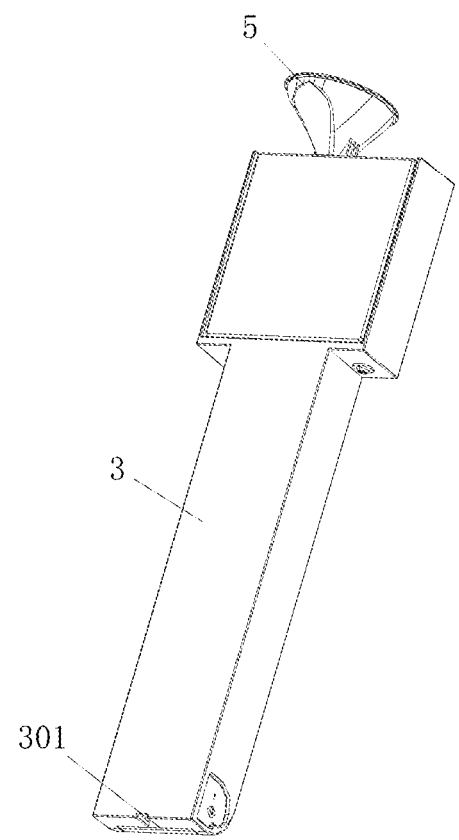
FIG. 5 is a schematic structure view of the the connecting arm and the air mouthpiece in assembled state according to one embodiment of the present application.

In particular, when the base 1 is a base having a side wall on which the first lug 11 and the second lug 12 are provided at interval and the other end of the connecting arm 3 is rotatably connected between the first lug 11 and the second lug 12, the inside of the base 1 can be provided with a first wiring chamber for laying the cables therein. As shown in FIGS. 3 and 4, the side wall of the base 1 is provided with a clearance opening 103 for providing a clearance to the rotation of the connecting arm 3. The clearance opening 103 is positioned between the first lug 11 and the second lug 12. As shown in FIG. 5, a second wiring chamber 304 for laying cables therein is provided inside the connecting arm 3, and a cable outlet 301 in communication with the second wiring chamber 304 is provided at the other end of the connecting arm 3. The cable outlet 301 extends from the end face of the other end of the connecting arm 3 to the side of the connecting arm 3, so that the portion of the cable outlet 301 located on the side of the connecting arm 3 is opposite to the clearance opening 103 when the connecting arm 3 is rotated to a first limit position; and the portion of the cable outlet 301 located on the end face of the connecting arm 3 is opposite to the clearance opening 103 when the connecting arm 3 is rotated to a second limit position.

By adopting the above configuration, when the connecting arm 3 is rotated between the first limit position and the second limit position, the cables can be constantly positioned at the portion of the cable outlet 301 opposite to the clearance opening 103, and thus the phenomenon of the cables being clipped and damaged can be avoided when the cables are positioned at the junction of the connecting arm 3 and the base 1.

Further, as shown in FIG. 1, when the connecting arm 3 is rotated to the first limit position, one end of the connecting arm 3 approaches the mounting seat 2 and abuts against the mounting seat 2, so that the alcohol detector 100 has a relatively compact overall structure when the connecting arm 3 is at the first limit position, providing convenient transportation. It is to be noted here that, this end of the connecting arm 3 is the end at which the breathing opening for alcohol detection 302 is provided.

The face information acquiring module 21 can comprise a camera through which the face information of a subject is acquired. In particular, the camera can be a commercially available camera so that it is convenient to obtain and deploy.

Figure 8:
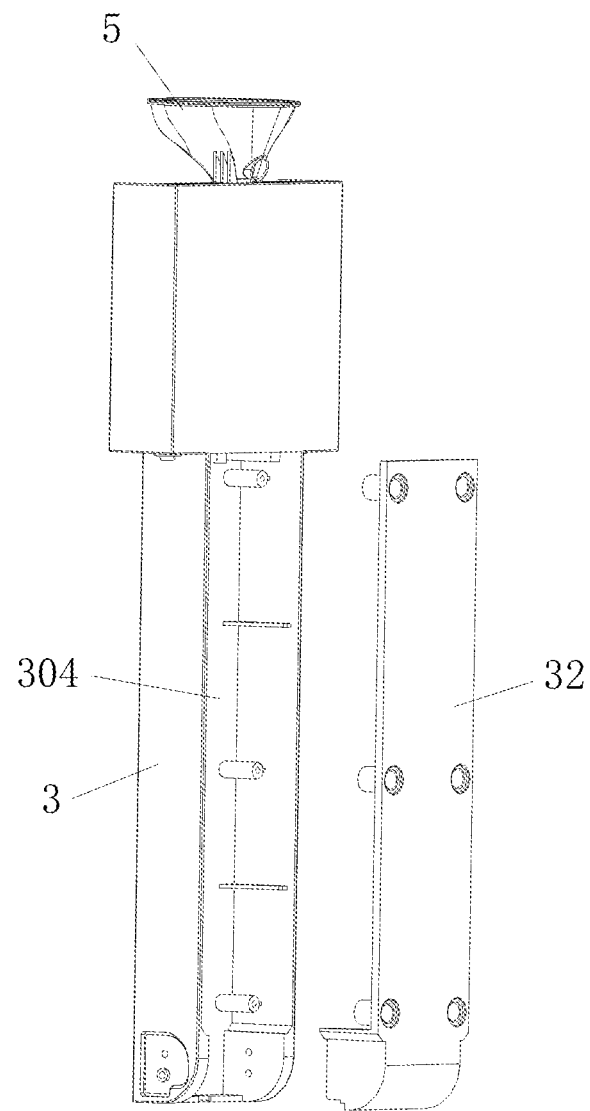
FIG. 8 is a schematic partially exploded structure view of the the connecting arm according to one embodiment of the present application.

Further, as shown in FIG. 8, the connecting arm 3 can have a cover plate 32, which is used for opening/closing the second wiring chamber 304. In particular, the cover plate 32 can be screwed at the opening of the second wiring chamber 304, so that the cover plate 32 can be detachable with regard to the opening of the second wiring chamber 304.

By adopting the above technical solution, when the cover plate 32 is opened, it is convenient for an operator to lay cables inside the second wiring chamber 304.

As shown in FIGS. 1 and 2, a stand 4 can be provided on the base 1 for providing a support for the mounting seat 2. The mounting seat 2 can be rotatably provided on the stand 4 so as to be connected with the base 1 via the stand 4. In this example, the mounting seat 2 can be rotated relative to the base 1, therefore, the position of the face information acquiring module 21 on the mounting seat 2 can be adjusted, so as to be adapted for the purpose of face recognition while different subjects are subject to breathing for detection.

By adopting the above configuration, since both the mounting seat 2 and the connecting arm 3 can be rotated relative to the base 1, it is convenient to adjust the positions of both the face information acquiring module 21 and the breathing opening for alcohol detection 302, so that the face information acquiring module 21 can synchronously perform face recognition to a subject while the subject is breathing into the breathing opening for alcohol detection 302, making the alcohol detector according to the present application versatile.

Figure 6:
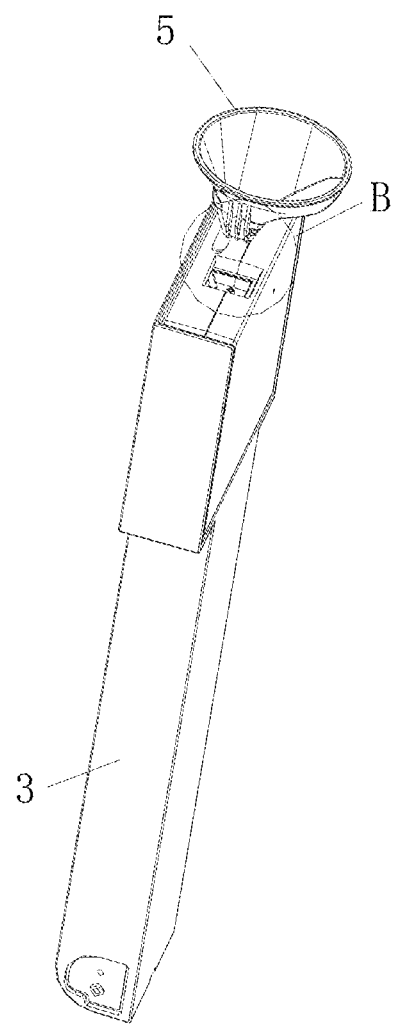
FIG. 6 is a schematic structure view of the connecting arm and the air mouthpiece in separate state according to one embodiment of the present application.
Figure 7:
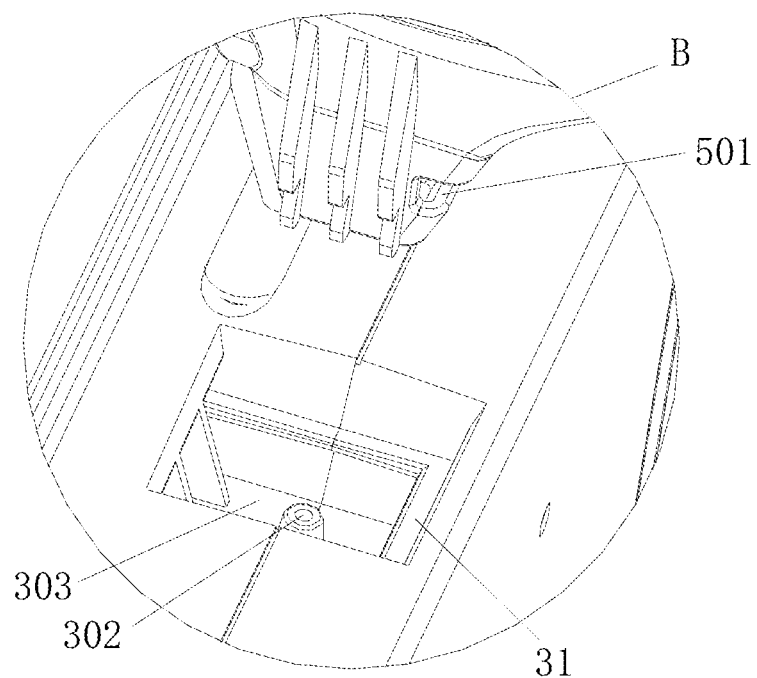
FIG. 7 is an enlarged schematic structure view of portion B in FIG. 6.

As shown in FIGS. 1 and 2, the alcohol detector 100 according to the present application can further comprise an air mouthpiece 5 used for breathing into the breathing opening for alcohol detection 302. As shown in FIGS. 6 and 7, a recess 303 is provided at one end of the connecting arm 3. The breathing opening for alcohol detection 302 is provided at the bottom of the recess 303, and a buckle 31 is provided on the side wall of the recess 303. A snap-in groove 501 is provided on the side of the air mouthpiece 5. One end of the air mouthpiece 5 is inserted into the recess 303, so that the buckle 31 is snap connected with the snap-in groove 501. In particular, when the air mouthpiece 5 is inserted into the recess 303, the buckle 31 on the side wall of the recess 303 is snap fixed into the snap-in groove 501 on the air mouthpiece 5. Since the air mouthpiece 5 is snap connected with the connecting arm 3, it can be disengaged from the connecting arm 3, so that the air mouthpiece 5 can be replaced at any time when the air mouthpiece 5 is damaged.

The alcohol detector 100 according to the present application can further comprises an ID card reading module, which is used for reading the ID information on an ID card and sending the obtained ID information to a storage device for storing and investigating in the future.

In particular, the structure of the ID card reading module can be selected from conventional ones in the art, and thus will be not described here.

In one embodiment, the present application further provides a gate system, which can comprise an intelligent identity-authentication alcohol detector 100 according to any of the above examples.

In the above example, due to the intelligent identity-authentication alcohol detector 100 provided in the gate system, when a subject breathes into the breathing opening for alcohol detection, the face information acquiring module 21 can constantly acquire the face information of the subject, so as to prevent the subject from cheating.

In particular, the above gate system comprises a gate, a control device and a motor used for controlling the opening/closing of the gate. The control device is used for controlling the opening/closing of the gate via the motor according to the detection results of the alcohol detecting module.

In particular, when the detection result from the alcohol detecting module shows that a subject did not have a drink, the control device sends an opening signal to the motor, which opens the gate according to the opening signal. When the detection result from the alcohol detecting module shows that an subject had a drink, the control device sends a closing signal to the motor, which closes the gate according to the closing signal.

The control device can be a microprocessor, PLC, or the like.

The face information acquiring module 21 on the alcohol detector 100 can acquire the face information of a subject. For example, when the face information acquiring module 21 comprises a camera, the face of a subject can be photoed over all the time by the camera, and the photographs taken at different time periods during the detection are sent by the camera to a backend and shown on the display of the backend, so that a guard for the gate can confirm whether the subject is cheating during the alcohol detection. When it is found that the subject is cheating during the alcohol detection, the guard can control the opening/closing of the gate on his own.

The alcohol detector 100 can comprise a storage device, in which the face information acquired by the face information acquiring module 21 can be stored, serving the function of recording the face information of a subject for inquiring in the future.

Further, the alcohol detector 100 can further comprise a face information storage module and a face recognition module. The face recognition module is used for comparing the face information acquired by the face information acquiring module 21 with each of the face information in the face information storage module and sending a signal for opening or closing the gate to the motor according to the comparison results.

In particular, when the face recognition module recognizes that the face information as acquired has been stored in the face information storage module, the face recognition module sends a signal for opening the gate to the motor; and when the face recognition module recognizes that the face information as acquired has not been stored in the face information storage module, the face recognition module sends a signal for closing the gate to the motor.

By adopting the above configuration, only scheduled persons can be accessible to the gate, and thus it can be applied to some occasions where a relatively high safety is required.

It is to be noted here that, the face information storage module can be a storage having face information stored therein. The particular structure of the face recognition module can be selected from conventional structures in the art, and thus will not be described here.

It is to be noted that, in the absence of conflict, the relevant technical features in the above examples can be combined with each other by those skilled in the art depending on actual needs, so as to achieve corresponding technical effects, the particular combinations of which are not provided here in details.

What is provided above is merely the preferred embodiments according to the present application, and the protection scope of the present application is not limited to the above embodiments. On the contrary, all the technical solutions obtained based on the concepts of the present application should fall within the protection scope of the present application. It should be noted that, for those skilled in the art, some improvements and modifications can be made without departing from the principles of the present applications, which should be also considered as falling within the protection scope of the present application.

What is claimed is:

1. An intelligent identity-authentication alcohol detector, characterized in comprising a base (1), a mounting seat (2), and a connecting arm (3);
   the mounting seat (2) is provided on the base (1), and a face information acquiring module is provided on the mounting seat (2);
   the connecting arm (3) is rotatably provided on the base (1), and a breathing opening for alcohol detection (302) is provided on the connecting arm (3); and the connecting arm (3) is used for driving the breathing opening for alcohol detection (302) to a position where the face information acquiring module acquires the face information of a subject, for the subject to breathe into the breathing opening for alcohol detection;
   wherein a first lug (12) and a second lug (12) are disposed at interval on the side wall of the base (1);
   the breathing opening for alcohol detection (302) is provided at one end of the connecting arm (3), and the other end of the connecting arm (3) is positioned between the first lug (11) and the second lug (12);
   one side of the connecting arm (3) is connected to the first lug (11) via a first rotary shaft, and the other side thereof is connected to the second lug (12) via a second rotary shaft;
   the axes of both the first rotary shaft and the second rotary shaft are collinear.

2. The intelligent identity-authentication alcohol detector according to claim 1, characterized in further comprising a limiting structure,
   the limiting structure is used for limiting the position of the connecting arm (3), so that the connecting arm (3) is rotated within a limited range.

3. The intelligent identity-authentication alcohol detector according to claim 2, characterized in that,
   the limiting structure comprises a first limiting post provided at one side of the connecting arm (3), a first limiting slot (101) extending along a first arc curve is provided on the first lug (11), the center of circle of the first arc curve is on the axis of the first rotary shaft, and the first limiting post is inserted into the first limiting slot (101), and is used for being driven by the connecting arm (3) to move along the first limiting slot (101);
   and/or, the limiting structure comprises a second limiting post provided at the other side of the connecting arm (3), a second limiting slot (102) extending along a second arc curve is provided on the second lug (12), the center of circle of the second arc curve is on the axis of the second rotary shaft, and the second limiting post is inserted into the second limiting slot (102), and is used for being driven by the connecting arm (3) to move along the second limiting slot (102).

4. The intelligent identity-authentication alcohol detector according to claim 1, characterized in further comprising an alcohol detecting module and a displaying module;
   the alcohol detecting module is provide on the connecting arm (3), and is used for detecting the level of alcohol in the air breathed into the breathing opening for alcohol detection (302);
   the displaying module is provided on the mounting seat (2), and connected with the alcohol detecting module via a cable; and the displaying module is used for receiving detected data from the alcohol detecting module and displaying the same;
   wherein the cables are laid inside of the connecting arm (3) and the base (1).

5. The intelligent identity-authentication alcohol detector according to claim 4, characterized in that,
   when the first lug (11) and the second lug (12) are provided at interval on the side wall of the base (1) and the other end of the connecting arm (3) is rotatably connected between the first lug (11) and the second lug (12), the inside of the base (1) has a first wiring chamber for laying the cables therein, the side wall of the base (1) is provided with a clearance opening (103) for providing a clearance to the rotation of the connecting arm (3), the clearance opening (103) being positioned between the first lug (11) and the second lug (12);
   a second wiring chamber (304) for laying cables therein is provided inside the connecting arm (3), and a cable outlet (301) in communication with the second wiring chamber (304) is provided at the other end of the connecting arm (3);
   the cable outlet (301) extends from the end face of the other end of the connecting arm (3) to the side of the connecting arm (3), so that the portion of the cable outlet (301) located on the side of the connecting arm (3) is opposite to the clearance opening (103) when the connecting arm (3) is rotated to a first limit position; and the portion of the cable outlet (301) located on the end face of the connecting arm (3) is opposite to the clearance opening (103) when the connecting arm (3) is rotated to a second limit position.

6. The intelligent identity-authentication alcohol detector according to claim 5, characterized in that,
when the connecting arm (3) is rotated to the first limit position, one end of the connecting arm (3) approaches the mounting seat (2) and abuts against the mounting seat (2).

7. The intelligent identity-authentication alcohol detector according to claim 5, characterized in that,
the connecting arm (3) has a cover plate (32) for opening/closing the second wiring chamber (304).

8. The intelligent identity-authentication alcohol detector according to claim 1, characterized in that,
a stand (4) is provided on the base (1) for providing a support for the mounting seat (2);
the mounting seat (2) is rotatably provided on the stand (4) so as to be connected with the base (1) via the stand (4).

9. The intelligent identity-authentication alcohol detector according to claim 1, characterized in further comprising an air mouthpiece (5) used for breathing into the breathing opening for alcohol detection (302);
a recess (303) is provided at one end of the connecting arm (3), the breathing opening for alcohol detection (302) is provided at the bottom of the recess (303), and a buckle (31) is provided on the side wall of the recess (303);
a snap-in groove (501) is provided on the side of the air mouthpiece (5), with one end of the air mouthpiece (5) being inserted into the recess (303) so that the buckle (31) is snap connected with the snap-in groove (501).

\* \* \* \* \*